US009005176B2

(12) United States Patent  
Saito

(10) Patent No.: US 9,005,176 B2  
(45) Date of Patent: Apr. 14, 2015

(54) ABSORBENT PAD

(75) Inventor: Tetsuhiro Saito, Sakura (JP)

(73) Assignee: Daio Paper Corporation, Ehime (JP)

( * ) Notice: Subject to any disclaimer, the term of this patent is extended or adjusted under 35 U.S.C. 154(b) by 519 days.

(21) Appl. No.: 12/918,128

(22) PCT Filed: Feb. 9, 2009

(86) PCT No.: PCT/JP2009/052153
§ 371 (c)(1),
(2), (4) Date: Aug. 18, 2010

(87) PCT Pub. No.: WO2009/104490
PCT Pub. Date: Aug. 27, 2009

(65) Prior Publication Data
US 2010/0331803 A1 Dec. 30, 2010

(30) Foreign Application Priority Data

Feb. 18, 2008 (JP) .................................. 2008-035891

(51) Int. Cl.
*A61F 13/15* (2006.01)
*A61F 13/505* (2006.01)
*A61F 13/56* (2006.01)
*A61F 13/62* (2006.01)
*A61F 13/74* (2006.01)

(52) U.S. Cl.
CPC ........... *A61F 13/505* (2013.01); *A61F 13/5616* (2013.01); *A61F 13/56* (2013.01); *A61F 13/622* (2013.01); *A61F 13/74* (2013.01)

(58) Field of Classification Search
CPC ........... A61F 13/5512; A61F 13/5515; A61F 13/505; A61F 13/62; A61F 13/622; A61F 2013/8402

USPC ................ 604/385.03, 391, 385.02, 386
See application file for complete search history.

(56) References Cited

U.S. PATENT DOCUMENTS 5,807,371 A * 9/1998 Toyoda et al. ........... 604/385.29
6,451,000 B1 * 9/2002 Hayase et al. ........... 604/385.13

(Continued)

FOREIGN PATENT DOCUMENTS

| CN | 1913856 | 2/2007 |
| JP | 2003-210524 | 7/2003 |
| JP | 2003-250609 | 9/2003 |
| JP | 2004-129939 | 4/2004 |
| JP | 2005-287791 | 10/2005 |

OTHER PUBLICATIONS

International Search Report for WO2009/104490.

(Continued)

*Primary Examiner* — Lynne Anderson
*Assistant Examiner* — Bradley Philips
(74) *Attorney, Agent, or Firm* — Renner, Kenner; Arthur M. Reginelli

(57) ABSTRACT

[Problem] To provide an absorbent pad that can be easily unstuck from a diaper or lower-body underwear
[Means for Solving Problem] An absorbent pad 200 where a hook tape 32 is exposed on an outer surface of the absorbent pad 200 configured by forming an attachment panel 31, that can be divided, via a folding portion 31c, into an extended portion 31a provided with the hook tape 32 formed on the top surface side thereof and a base portion 31b fixed to an outer sheet 25; and by folding back the attachment panel 31 via the folding portion 31c such that the extended portion 31a is layered on the base portion 31b side.

17 Claims, 19 Drawing Sheets

(56) References Cited

U.S. PATENT DOCUMENTS

| | | | |
|---|---|---|---|
| 7,037,457 B2 * | 5/2006 | Seidel et al. | 264/267 |
| 2005/0177125 A1 | 8/2005 | Kondo | |
| 2007/0173781 A1 * | 7/2007 | Jackson et al. | 604/391 |
| 2007/0197995 A1 * | 8/2007 | Neugebauer et al. | 604/389 |
| 2008/0097368 A1 * | 4/2008 | Molander | 604/391 |
| 2009/0043275 A1 * | 2/2009 | Perneborn | 604/391 |
| 2009/0062759 A1 * | 3/2009 | Shimada et al. | 604/365 |

OTHER PUBLICATIONS

JP 2003-210524 English Abstract.
JP 2003-250609 English Abstract.
JP 2004-129939 English Abstract.
JP 2005-287791 English Abstract.

* cited by examiner

← Back direction    Front direction→

(a)

(b)

(c)

ABSORBENT PAD

TECHNICAL FIELD

The present invention relates to absorbent pads used for absorbing excretion such as urine, menstrual blood, and the like.

BACKGROUND ART

For example, disposable diapers for adults generally have absorbent pads on inner surfaces for the purpose of absorbing urine in consideration of the frequency of replacement (refer to Patent Document 1 or 2, for example). In addition, lower-body underwear also has absorbent pads attached on inner surfaces.

Such absorbent pads each include a liquid impervious sheet, a liquid pervious top sheet, and an absorbent body interposed between the two sheets. The liquid impervious sheet and the liquid pervious top sheet are each extended beyond a ventral side end and a back side end of the absorbent body. Those extended portions form a front end flap portion and a rear end flap portion in the absence of the absorbent body. The absorbent pad has a ventral side portion extending from a crotch portion to the ventral side and a back side portion extending from the crotch portion to the back side.

In addition, the absorbent pad with such a structure as stated above generally has on an underside surface, a pressure sensitive adhesive or a hook tape of an hook and loop fastener (mechanical fastener) or the like, for the purpose of preventing the absorbent pad from being displaced while the diaper is used, and the absorbent pad is attached via any of those attachment means to the inner side surface of the diaper or the lower-body underwear. Among the foregoing attachment means, the attachment means using a hook tape has an advantage of not being decreased in attachment capability even after repeated actions of attachment and detachment.

Absorbent pads may be replaced in various manners. When the wearer or the helper replaces a used absorbent pad with a new one, the wearer or the helper generally pulls down the diaper or the lower-body underwear a certain amount and then removes the absorbent pad from the diaper or the lower-body underwear.

Patent Document 1: JP 2005-287791 A
Patent Document 2: JP 2003-210524 A

DISCLOSURE OF THE INVENTION

Technical Problem to be Solved

However, the conventional absorbent pad simply with a hook tape on the underside surface requires a significantly wide space for removing the absorbent pad from a diaper or lower-body underwear at the time of replacement. Accordingly, the diaper or the lower-body underwear needs to be pulled down to near the knees of the wearer, which makes the replacement troublesome.

Because of such troublesome replacement, in some cases of removing the used absorbent pad, the diaper or the lower-body underwear is hardly pulled down and the absorbent pad is picked up at the ventral side and pulled out from the diaper or the lower-body underwear. However, if the conventional absorbent pad is replaced in such a manner, when the absorbent pad is pulled out, mostly a shearing force acts on an attachment plane between the hook tape and the diaper or the lower-body underwear. The hook tape is extremely hard to detach from the nature thereof and requires a strong force for detachment. Even if the hook tape is unstuck, the diaper or the lower-body underwear is subjected to a strong force, and therefore projections on the hook tape cause damage to fibers of the diaper or the lower-body underwear. Nevertheless, it cannot be said to be a favorable solution to weaken the adhesive power of the hook tape to decrease a force required for detachment because the hook tape is lowered in capability of displacement prevention.

Therefore, a main object of the present invention is to provide an absorbent pad that has a sufficient capability of displacement prevention and can be easily unstuck from a diaper or lower-body underwear without causing damage to the diaper or the lower-body underwear at the time of replacement.

Means to Solve the Problems

The present invention solving the foregoing issue is as follows.

<Invention According to Claim 1>

An absorbent pad having a ventral side portion extending from a crotch portion to a ventral side and a back side portion extending from the crotch portion to a back side, comprising:

an attachment panel including: a base portion fixed to an underside surface of the absorbent pad; an extended portion that extends from a rear edge of the base portion and is unfixed to the underside surface of the absorbent pad; and a hook tape that is fixed to the extended portion on a surface thereof which is the same side as the surface of the base portion fixed to the absorbent pad and that has a large number of hook shaped projections on an opposite of the fixed surface, wherein the extended portion of the attachment panel is folded back frontward within a range from a boundary with the base portion to a part of the hook tape and is configured such that the surface of the hook tape with the hook shaped projections is exposed on an outer surface of the folded portion.

(Effect and Operation)

For attachment of the absorbent pad of the present invention, the attachment panel is folded back, and the hook shaped projections of the hook tape exposed on the outer surface of the folded portion are attached to the inner surface of the diaper or the lower-body underwear. In such an attachment state, when the absorbent pad is picked up at the front end portion and pulled out from the ventral side for replacement, the folded portion of the attachment panel including the attached portion of the hook tape is unstuck as if to be peeled off gradually from the base portion. At that time, a force acts on the attachment plane of the hook tape, not in a direction of shearing but in a direction orthogonal to the direction of shearing. This allows the hook tape to be smoothly unstuck from the attachment plane with a weaker force. Accordingly, the absorbent pad can be easily removed from the diaper or the lower-body underwear for replacement without the need to pull down the diaper or the lower-body underwear so much. In addition, the absorbent pad of the present invention requires no strong shearing force to act on the attachment plane, which causes no damage to the attachment plane of the diaper or the lower-body underwear. Further, the absorbent pad of the present invention eliminates the need for decreasing the hook tape in adhesive power and therefore will not be deteriorated in capability of displacement prevention.

<Invention According to Claim 2>

The absorbent pad according to Claim 1, wherein, in the folded state, the folded portion is temporarily tacked to an opposite surface thereof in a detachable manner.

(Effect and Operation)

When the folded portion of the attachment panel is not absolutely fixed to the opposite surface, the absorbent pad can be attached to the diaper or the like for use but the absorbent pad may be displaced at the folded portion of the attachment panel. Therefore, it is preferable to tack the folded portion temporarily to the opposite surface thereof in a detachable manner to prevent the absorbent pad from being displaced during use, as recited in this claim. Accordingly, when the absorbent pad is replaced, the folded portion of the attachment panel is peeled off to remove the temporarily tacked absorbent pad, which does not deteriorate the foregoing effect and operation of the present invention.

<Invention According to Claim 3>

The absorbent pad according to Claim 1 or 2, wherein the attachment panel is provided at the back side portion.

(Effect and Operation)

It is preferable that the attachment panel of the present invention is provided particularly on the back side that is hard to reach by hand, as recited in this claim.

<Invention According to Claim 4>

The absorbent pad according to any one of Claims 1 to 3, wherein, when the folded portion of the attachment panel is unfolded backward, the entire surface of the hook tape having the hook shaped projections is opposed to the underside surface of the absorbent pad, so as not to be exposed to the body of a wearer.

(Effect and Operation)

In such a configuration as recited in this claim, when the absorbent pad is replaced, the folded portion of the attachment panel is peeled off. Therefore, the entire hook tape is not exposed to the body of the wearer even if the entire attachment panel is unfolded. This makes it possible to prevent a situation where the hook tape of hard material causes damage to the skin of the wearer.

<Invention According to Claim 5>

The absorbent pad according to any one of Claims 1 to 4, wherein the hook shaped projections incline toward a leading edge of the extended portion.

(Effect and Operation)

In the foregoing configuration where the attachment panel is provided on the back side portion, when the hook shaped projections of the hook tape incline in such a manner, even if the back side portion of the absorbent pad is about to slip off toward the crotch portion, the hook shaped projections become stuck deep in the attachment plane. This makes such slippage less prone to occur (this slippage is likely to occur in particular when the back side portion becomes heavy due to absorption of excretion). Further, in the present invention, when the absorbent pad is picked up at the front end portion and pulled out from the ventral side for replacement of the absorbent pad, the folded portion of the attachment panel is unstuck as if to be peeled off gradually from the base portion, and therefore using the inclined hook shaped projections as recited in this claim does not deteriorate ease of detachment.

Effect of the Invention

According to the present invention as stated above, it is possible to advantageously provide an absorbent pad that has a sufficient capability of displacement prevention and can be easily unstuck from a diaper or lower-body underwear without causing any damage to the diaper or the lower-body underwear at the time of replacement.

BEST MODE FOR CARRYING OUT THE INVENTION

One embodiment of the present invention will be described below taking a urine absorbent pad as an example, although the present invention is also applicable to other kinds of absorbent pads such as sanitary napkins. In the following description, the "crotch portion" refers to a portion of an absorbent pad that fits to the crotch of a wearer while using, and constitutes a central portion in a front-back direction and its front-back neighborhood portions in most products. Specifically, in each of products for adults, the crotch portion has a range ±150 mm of the central portion of the product in the front-back direction. In addition, the "ventral side portion" and "front side portion" refer to a portion in front of the crotch portion, and the "back side portion" and "rear side portion" refer to a portion in back of the crotch portion.

(Tape-Type Disposable Diaper)

FIGS. 1 to 6 show one example of a tape-type disposable diaper 100 for the present invention. The disposable diaper 100 has a liquid impervious back sheet 1 with an outer sheet 12 layered on an outer surface thereof, a liquid pervious top sheet 2, and an absorbent body 3 interposed between an inner surface of the liquid impervious back sheet 1 and the liquid pervious top sheet 2.

The liquid impervious back sheet 1 may use a polyethylene film, or may use any other sheet having moisture permeability without deteriorating in water imperviousness, from the viewpoint of prevention of stuffiness. The water-impervious and moisture-permeable sheet may be a microporous sheet obtained by melting and kneading an inorganic filling material into an olefin resin such as polyethylene, polypropylene or the like to thereby form a sheet and then extending the sheet in a uniaxial or biaxial direction, for example. Preferably, the back sheet 1 has a weight of 13 to 40 g/m$^2$ per unit area and a thickness of 0.01 to 0.1 mm.

The outer sheet 12 may use any of various nonwoven fabrics. Raw materials for constituting the nonwoven fabric may be any of synthetic fibers based on olefin such as polyethylene or polypropylene, polyester, amide or the like, recycled fibers such as rayon or cupra, natural fibers such as cotton or the like. Preferably, a nonwoven fabric for use in the outer sheet 12 has a fiber basis weight of 13 to 30 g/m$^2$ and a thickness of 0.05 to 1 mm.

The liquid pervious top sheet 2 uses a porous or nonporous nonwoven fabric. Raw materials for constituting the nonwoven fabric may be any of synthetic fibers based on olefin such as polyethylene or polypropylene, polyester, amide or the like, recycled fibers such as rayon or cupra, natural fibers such as cotton or the like. Preferably, a nonwoven fabric for use in the liquid pervious top sheet 2 has a fiber basis weight of 15 to 30 g/m$^2$ and a thickness of 0.05 to 1 mm. Forming the liquid pervious top sheet 2 by a nonwoven fabric as stated above makes it possible to attach hook tapes as described later.

Basically the absorbent body 3 uses an accumulated body of pulp fibers, an assembly of filaments of cellulose acetate or the like, or a nonwoven fabric, to which high-absorbent polymers may be mixed and fixed as required. If necessary, the absorbent body 3 may be wrapped with crepe paper (not shown). The absorbent body 3 can be formed in any of appropriate shapes, and preferably has the shape of a sandglass as illustrated or a rectangle or the like, which extends from the front to back sides of the crotch portion. The absorbent body 3 has desirably a basis weight of pulp of about 100 to 500 g/m$^2$ and a thickness of about 1 to 15 mm. In addition, a desired basis weight of high-absorbent resin is about 0 to 300 g/m$^2$. If a rate of high-absorbent resin content is too low, it is impossible to provide the absorbent body 3 with sufficient absorbent performance. In contrast, if a rate of high-absorbent resin content is too high, the absorbent body 3 is likely to be twisted or broken because there is no engagement between pulp fibers.

The liquid impervious back sheet 1 extends outward beyond the circumference of the absorbent body 3, and is formed in the shape of an approximate rectangle. To entire inner surfaces of side extended portions of the liquid impervious back sheet 1, widthwise outside sections 4x of barrier sheets 4 are stuck in the front-back direction, thereby forming side flap portions SF in the absence of the absorbent body 3. The barrier sheets 4 have widthwise central sections 4c extending to an upper side of the top sheet 2. At ends of the widthwise central sections 4c, elongated resilient and elastic members 4G are fixed in a stretched state in the front-back direction with a hot-melt adhesive or the like. The elongated resilient and elastic members 4G and elongated resilient and elastic members 13 described later may be formed in the shape of a thread, a string, a band, or the like, and use any of commonly used materials such as styrene-based rubber, olefin-based rubber, urethane-based rubber, ester-based rubber, polyurethane, polyethylene, polystyrene, styrene-butadiene, silicon, polyester, or the like.

The liquid pervious top sheet 2 has the shape of a sandglass slightly larger than the absorbent body 3. The liquid pervious top sheet 2 has sections extending outward slightly beyond the side edges of the absorbent body 3. The extended sections are interposed between the barrier sheets 4 and the liquid impervious back sheet 1 and are fixed to the liquid impervious back sheet 1 with a hot-melt adhesive or the like. FIGS. 3 and 4 show those fixed sections in a dot pattern. The barrier sheets 4 may use a material of a plastic sheet or a melt-blown nonwoven fabric, and preferably use a nonwoven fabric made water-repellent by silicon or the like, from the viewpoint of a favorable texture.

If an outer surface of the liquid impervious back sheet 1 is covered with a nonwoven fabric, the outer nonwoven fabric, instead of the liquid impervious back sheet 1, may extend outward beyond the circumference of the absorbent body 3 to form the side flap portions SF in the absence of the absorbent body 3 together with the side portions of the barrier sheets 4. In this case, the liquid impervious back sheet 1 may not extend to the side flap portions SF so as to have the same shape as that of the top sheet 2.

As shown in FIGS. 3 and 4, the two barrier sheets 4 and 4 are fixed in such a manner that the widthwise outside sections 4x are fixed undetachably to the entire front-back inner surface of the article (in the illustrated embodiment, the top surface of the top sheet 2 and the inner surface of the back sheet 1); the widthwise central sections 4c are undetachably fixed at both front-back ends to the inner surface of the article (in the illustrated embodiment, the top surface of the top sheet 2); and the widthwise central sections 4c are not fixed between the both front-back ends to the inner surface of the article (in the illustrated embodiment, the top surface of the top sheet 2). Those unfixed sections constitute barrier sections that can be erected with respect to the inner surface of the article (in the illustrated embodiment, the top surface of the top sheet 2). The barrier sections have erected base ends 4b located in boundaries between the widthwise outside fixed sections 4x and the inner sections 4c in the barrier sheets 4.

At the both front-back ends of the disposable diaper 100, the liquid impervious back sheet 1 and the liquid pervious top sheet 2 extend toward both front-back sides beyond the front-back ends of the absorbent body 3, thereby to form end flap portions EF in the absence of the absorbent body 3. Each of the back-side end flap portion EF has a plurality of, three in the illustrated embodiment, threadlike resilient and elastic members 7, 7 . . . disposed in the width direction. The threadlike resilient and elastic members 7 may use any of commonly used materials such as styrene-based rubber, olefin-based rubber, urethane-based rubber, ester-based rubber, polyurethane, polyethylene, polystyrene, styrene-butadiene, silicon, polyester, or the like.

In addition, the both side flap portions SF of the back side B1 have fastening tapes 5 and 5 projecting sideward around the waist portion. In addition, the ventral side F1 of the disposable diaper 100 has a front target tape 6 in the width direction on a surface thereof around the waist portion. The fastening tapes 5 have attachment pieces 8a attached to the front target tape 6 so that the disposable diaper 100 fits to the body of the wearer.

Each of the fastening tapes 5 in the illustrated example is attached to the disposable diaper 100 at an inner end of a fastening base sheet 8, and has the two attachment pieces 8a and 8a at a leading end thereof. The two attachment pieces 8a extend from an outer edge and project sideward in a vertically aligned manner. In addition, the fastening base sheets 8 each have perforation 10 between the attachment pieces 8a and 8a formed in a horizontal direction inward from the outer edge thereof. However, the fastening tapes 5 are not limited to the foregoing arrangement and may be any of publicly known fastening tapes. The fastening base sheets 8 may use any of various sheet materials, and preferably use a single-layer or multi-layer nonwoven fabric with a basis weight of 40 to 80 g/m$^2$. A preferred processing method for the nonwoven fabric is a spun-bonding method with an excellent strength property. The attachment pieces 8a and 8a have on inner surfaces thereof (the liquid pervious top sheet 2 side) hook tapes (hook materials of mechanical fasteners) 9 and 9 having a large number of hook shaped projections on surfaces thereof. The hook shaped projections can be attached to front target tapes 6 (loop materials of mechanical fasteners) on surfaces of which the hook shaped projections engage in a detachable manner.

Characteristically, a plurality of elongated resilient and elastic members 13 is provided on the underside surface of the absorbent body 3 at the both sides of the diaper 100 in the width direction so as to extend from the ventral side portion F1 to the back side portion B1 and to bulge at the crotch portion C1 toward the center in the width direction. In this embodiment, the elongated resilient and elastic members 13 are fixed using an adhesive between the outer sheet 12 and the back sheet 1, and alternatively the elongated resilient and elastic members 13 may be fixed to the inner surface of the back sheet 1.

Particularly in this embodiment, a plurality of outer resilient and elastic members 13s (five in the illustrated example) is provided at the side flap portions SF so as to extend along the narrowed parts around the leg portions. In addition, a plurality of inner resilient and elastic members 13i (three in the illustrated example) is also provided at the side flap portions SF, having start and end points at the side flap portions SF on the ventral and back sides. The inner resilient and elastic members 13i bulge and extend inward at the crotch portion C1 so as to overlap the absorbent body 3.

The inner resilient and elastic members 13i are shifted outward in the width direction with distance from the crotch portion C1. The inclination of the shifted inner resilient and elastic member 13i (in the front-back direction) is steeper at the portion extended to the back side than at the portion extended to the ventral side. The inner resilient and elastic members 13i are arranged so as to come close to the outer resilient and elastic members 13s and then extend along the outer resilient and elastic members at specific intervals.

At the crotch portion C1, a minimum widthwise interval d1 between the inner resilient and elastic member 13i on one widthwise side and the inner resilient and elastic member 13i on the other widthwise side can be decided as appropriate, and preferably is 10 to 150 mm. If the interval d1 is too short, the inner resilient and elastic members 13i are prone to overlap a resilient and elastic member 24G described later on the absorbent pad 200 or to overlap the same by an increased area. In contrast, if the interval d1 is too long, the inner resilient and elastic members 13i overlap the widthwise both sides of the absorbent pad 200 by a decreased area or do not overlap the same at all. In either case, the absorbent pad 200 may be less effective in enhancing a fit property.

The elongated resilient and elastic members 13s and 13i may use synthetic or natural rubber having any of appropriate shapes such as a thread, a string, a band, and the like. If synthetic rubber is used for the elongated resilient and elastic members, the elongated resilient and elastic members have preferably a fineness of about 400 to 1,200 dtex and an extension ratio of about 180 to 300%. In addition, it is preferable to arrange about one to ten outer resilient and elastic members 13s in parallel at intervals of 2 to 10 mm, and arrange about one to ten inner resilient and elastic members 13i in parallel at intervals of 2 to 15 mm.

(Absorbent Pad)

FIGS. 7 to 15 show an example of an absorbent pad 200 of the present invention. The absorbent pad 200 is intended for use on an inner surface of a disposable diaper 100. The absorbent pad 200 has a crotch portion C2, a ventral side (front side) portion F2 and a back side (rear side) portion B2 extending on both sides of the crotch portion C2 in the front-back direction. Dimensions of those portions can be decided as appropriate. For example, a full length (front-back length) L1 of the article may be about 350 to 700 mm, a full width W1 of the same may be about 130 to 400 mm (however, W1 is narrower than a width of an absorbent surface of the diaper). In this case, a front-back length of the crotch portion C2 may be about 10 to 150 mm, a front-back length of the ventral side portion F2 may be about 50 to 350 mm, and a front-back length of the back side portion B2 may be about 50 to 350 mm.

The absorbent pad 200 has a basic structure in which an absorbent body 23 is interposed between an inner surface of a liquid impervious back sheet 21 and a liquid pervious top sheet 22. Basically, the absorbent body 23 uses an accumulated body of pulp fibers, an assembly of filaments of cellulose acetate or the like, or a nonwoven fabric, to which high-absorbent polymers may be mixed and fixed as required. If necessary, the absorbent body 23 may be wrapped with crepe paper (not shown). The absorbent body 23 may be formed in any of appropriate shapes such as a band, a rectangle, a trapezoid, and the like, which is longer at a front side than a back side. A basis weight of fibers and a basis weight of absorbent polymers in the absorbent body 23 can be decided as appropriate. A preferred basis weight of fibers is about 100 to 600 g/m$^2$, and a preferred basis weight of absorbent polymers is about 0 to 400 g/m$^2$.

The liquid impervious back sheet 21 is disposed on an underside surface of the absorbent body 23 so as to extend beyond a circumferential edge of the absorbent body 23 by a predetermined length. The liquid impervious back sheet 21 may use a polyethylene film, or may use a sheet having moisture permeability without losing in water imperviousness, from the viewpoint of stuffiness prevention. The water-impervious and moisture-permeable sheet may be a microporous sheet obtained by melting and kneading an inorganic filling material into an olefin resin such as polyethylene, polypropylene or the like to thereby form a sheet and then extending the sheet in a uniaxial or biaxial direction, for example.

In addition, an outer (underside) surface of the liquid impervious back sheet 21 is covered with an outer sheet 25. The outer sheet 25 may use any of various nonwoven fabrics. Using such a nonwoven fabric makes it possible to fix the hook tape 32 to the outer sheet 25 when the hook tape 32 is unused, as described later. Raw materials for constituting the nonwoven fabric may be any of synthetic fibers based on olefin such as polyethylene or polypropylene, polyester, amide or the like, recycled fibers such as rayon or cupra, natural fibers such as cotton or the like.

The rectangular hook tape 30 is layered on an underside surface of the outer sheet 25 along an inside of a ventral side end edge of the absorbent body 23. The hook tape 30 has on an underside surface a large number of fine mushroom-like hook shaped projections erected toward the underside surface. The hook tape 30 can be detachably attached to the liquid pervious top sheet 2 by engaging the hook shaped projections with fibers of nonwoven fabric of the liquid pervious top sheet 2. The hook tape 30 can be sized as appropriate, and for example, may be about 50 mm to 200 mm in width length (but is shorter than the width of the diaper) and about 5 mm to 50 mm in front-back length.

A shape of the hook shaped projections may be any of a mushroom, a hook, a Japanese katakana character "レ (re)", a J letter, a T letter, a double-J letter (in which two J's are joined back to back) and the like. The hook tape 30 can be attached with a hot-melt adhesive or the like. A layer of a pressure sensitive adhesive may be formed on the hook tape 30 by applying an adhesive solidly or in a pattern through scattering or the like.

A top surface of the absorbent body 23 is covered with the liquid pervious top sheet 22. In the illustrated embodiment, the absorbent body 23 partly extends beyond side edges of the top sheet 22, but the top sheet 22 may be made wider so that the absorbent body 23 does not extends at the side edges. The top sheet 22 uses a porous or nonporous nonwoven fabric, a perforated plastic sheet, or the like. Raw materials for constituting the nonwoven fabric may be any of synthetic fibers based on olefin such as polyethylene or polypropylene, polyester, amide or the like, recycled fibers such as rayon or cupra, natural fibers such as cotton or the like.

At both end portions of the absorbent pad 200 in the front-back direction, the outer sheet 12 and the liquid pervious top sheet 1 extend toward both front-back sides of the front and back ends of the absorbent body 23 and are stuck together to thereby form end flap portions EF in the absence of the absorbent body 23.

At both lateral sides of the absorbent pad 200, the liquid impervious back sheet 21 extends outward beyond the side edges of the absorbent body 23. In addition, widthwise outside sections 24x of barrier sheets 24 are stuck to entire inner surfaces of sections ranging from the extended portions of the liquid impervious back sheet 21 to side portions of the top sheet 22 in the front-back direction, thereby to form side flap portions SF in the absence of the absorbent body 23. Those stuck sections, as shown in a dot pattern in FIGS. 9 to 12, can be formed with a hot-melt adhesive or by heat sealing or ultrasonic sealing.

The absorbent pad 200 has a main portion BD constituted by a portion with interposition of the absorbent body other than the end flap portions EF and the side flap portions SF. In the illustrated embodiment, the front and back ends of the absorbent body 23 are linearly arranged along the width direction, and therefore boundaries BL between the front and back end flap portions EF and the main portion BD are also linearly arranged. These boundaries may be curved in the form of an arc or may be bent so as to turn downward or the like. The end flap portions EF can be sized as appropriate. Since each of the end flap portions EF is used for attachment of the pad 200 in the present invention, it is preferred that at least a part of the end flap portion EF extends beyond the boundary BL with the main portion BD by 10 mm or more. In addition, it is preferred that the end flap portions EF each have an area of about 2,000 to 12,000 mm$^2$.

The barrier sheets 24 may use a plastic sheet or a meltblown nonwoven fabric as a material, and preferably use a nonwoven fabric made water-repellent by silicon or the like, from the viewpoint of a favorable texture.

The barrier sheets 24 have widthwise central sections 24c extending to the upper side of the top sheet 22. At ends of the widthwise central sections 24c, elongated resilient and elastic members 24G are fixed in a stretched state in the front-back direction with a hot-melt adhesive or the like. The elongated resilient and elastic members 24G may be formed in the shape of a thread, a string, a band, or the like, and may use any of common materials such as styrene-based rubber, olefin-based rubber, urethane-based rubber, ester-based rubber, polyurethane, polyethylene, polystyrene, styrene-butadiene, silicon, polyester, or the like.

In the two barrier sheets 24 and 24, the widthwise outside sections 24x are stuck and fixed to the entire inner surface of the article (in the illustrated embodiment, the top surface of the top sheet 22 and the inner surface of the outer sheet 25) in the front-back direction, and the widthwise central sections 24c are stuck and fixed to the inner surface of the article (in the illustrated embodiment, the top surface of the top sheet 22) at the both ends in the front-back direction, and are not fixed to the inner surface of the article (in the illustrated embodiment, the top surface of the top sheet 22) between the both ends in the front-back direction. Those unfixed portions constitute barrier portions that can be erected with respect to the inner surface of the article (in the illustrated embodiment, the top surface of the top sheet 22), and the barrier portions have erected base ends 24b located in boundaries between the widthwise outside fixed sections 24x and the inside sections 24c in the barrier sheets 24, as shown in FIG. 10.

Characteristically, as shown in FIGS. 7 and 8, the outer sheet 25 has on the underside surface an attachment panel 31 composed of a multi-layer nonwoven fabric near at a back side end. The attachment panel 31 has at an intermediate portion in the front-back direction a folding portion 31c extending along the width direction. The attachment panel 31 is divided via the folding portion 31c into a back side extended portion 31a and a ventral side base portion 31b. The attachment panel 31 is arranged in such a manner that the folding portion 31c is positioned near the boundary BL. The attachment panel 31 may use any of various sheet materials. As the sheet material is higher in firmness, an attachment plane between a hook tape 32 described later and the liquid pervious top sheet 2 is increased in detachability. The sheet material is preferably a single-layer or multi-layer nonwoven fabric with a thickness of 50 μm to 500 μm and a basis weight of 15 to 100 g/m$^2$. The nonwoven fabric is preferably processed by a spun-bonding method with excellent strength properties.

The base portion 31b is stuck at a front surface to the outer sheet 25. The stuck portion, as shown in a dot pattern in FIG. 11, can be formed by a hot-melt adhesive, heat sealing, or ultrasonic sealing. The base portion 31b has a widthwise length slightly shorter than the width of the absorbent body 23, and is positioned at the inside of the absorbent body 23. In addition, the base portion 31b has on an underside surface a temporary tack portion 33 composed of a hot-melt adhesive. The temporary tack portion 33 can be attached to the underside surface of an extended portion 31a as described later. The temporary tack portion 33 is shown in FIGS. 8 and 11 in a wave-line pattern. The temporary tack portion 33 may be covered with a protection sheet (not shown). In that case, the temporary tack portion 33 is exposed by removing the protection sheet at the time of use.

The temporary tack portion 33 is weakened in adhesive power with respect to the extended portion 31a by about 50% than adhesive power of the hook tape 32 with respect to the top surface of the liquid pervious top sheet 2. Accordingly, when the absorbent pad 200 is pulled out as described later, the adhesive plane of the temporary tack portion 33 is detached earlier than the attachment plane of the hook tape 32.

The extend portion 31a has the hook tape 32 layered on the top surface thereof as shown in FIGS. 7, 8, and 12. The hook tape 32 has a large number of fine mushroom-like hook shaped projections erected toward the top surface, as in the case of the hook tape 30. The hook tape 32 can be detachably attached to the outer sheet 25 by engaging the hook shaped projections with fibers of nonwoven fabric of the outer sheet 25. When attached to the outer sheet 25, the extended portion 31a has a front-back length falling within the end flap portions EF. As another shape of hook shaped projections, the hook tape 32 may use the same hook shaped projections as those of the hook tape 30. Since the hook tape 32 is detachably attached to the outer sheet 25 as stated above, attaching the hook tape 32 to the outer sheet 25 when the hook tape 32 is unused makes it possible to prevent the hook shaped projections on the hook tape 32 from causing damage to the user or any adjacent product.

When the thus configured absorbent pad 200 is to be used, the attachment panel 31 is folded back via the folding portion 31c such that the underside surface of the extended portion 31a is layered on the underside surface of the base portion 31b, and the extended portion 31a on the underside surface of the base portion 31b is attached to the temporary tack portion 33, as shown in FIGS. 13 and 14. In addition, the absorbent pad 200 is attached to the top surface of the liquid pervious top sheet 2 of the diaper 100 by means of the hook tape 30 and the hook tape 32, as shown in FIG. 15.

After use, the thus attached absorbent pad 200 is removed from the diaper 100 by firstly detaching the ventral side hook tape 30, and then picking up the absorbent pad 200 at the ventral side and pulling out the absorbent pad 200 in the direction toward the ventral side. Accordingly, as shown in FIG. 16 (*b*), the adhesive plane between the temporary tack portion 33 of the hook tape 32 and the underside surface of the extended portion 31a is detached. Sequentially, as shown in FIG. 16 (*c*), the extended portion 31a of the attachment panel 31 is almost lifted at the folding portion 31c from the liquid pervious top sheet 2, whereby the extended portion 31a is virtually peeled off at the folding portion 31c side. That is, the attachment plane of the hook tape 32 is subjected to a force in the up-down direction, not in the shearing direction, which makes it possible to detach the attachment plane with a weak force.

Specifically, the absorbent pad 200 can be detached without having to apply a strong force to the attachment plane, which prevents the attachment plane of the diaper or the lower-body underwear from being damaged. In addition, there is no need to weaken the adhesive power of the hook tape 32, which prevents the hook tape 32 from being displaced or peeled off from the attachment plane due to movements of the wearer.

In addition, when the absorbent pad 200 is used, the extended portion 31a is attached to the temporary tack portion 33, which makes it possible to prevent that any change occurs in positional relationship between the attachment panel 31 and the liquid impervious back sheet 1 during use of the diaper 100. This also avoids the absorbent pad 200 being displaced from the diaper 100 due to movements of the wearer.

Other Embodiments

Next, other embodiments of the present invention will be described in detail with reference to the attached drawings.

As shown in FIG. 17, the attachment panel 31 may be formed so as to be shorter in widthwise length. In such a formation, when the absorbent pad 200 is detached from the diaper 100, the hook tape 32 is detached as if to be peeled off from the back side to the ventral side on the attachment plane between the hook tape 32 and the liquid pervious top sheet 2. This decreases the number of hook shaped projections detached at a time from the liquid pervious top sheet 2, thereby allowing the hook tape 32 to be easily peeled off.

In addition, as shown in FIG. 18, the attachment panel 31 may be provided in a plurality of locations. Providing the attachment panel 31 near the both ends of the back side as shown in FIG. 18 can shorten a sum total of widthwise length of the hook tape 32, thereby allowing the hook tape 32 to be easily peeled off as in the configuration of FIG. 17. This also prevents preferably that the absorbent pad 200 is peeled off from the both ends of the back side of the absorbent pad 200. In addition, providing the attachment panel 31 near at the center of the absorbent pad 200 can prevent the absorbent pad 200 from being displaced near at the center.

Further, as shown in FIG. 19, the hook shaped projections F may be formed so as to incline at an angle of $\theta_1$ with respect to the base material sheet 32s of the hook tape 32. Accordingly, when the attachment panel 31 is folded back, leading ends of the hook shaped projections F of the hook tape 32 are oriented frontward. In such a formation, the hook tape 32 is less prone to be subjected to a force in the shearing direction, as compared to the formation of the absorbent pad 200 in which the hook shaped projections F are erected perpendicular to the base material sheet 32s when the absorbent pad 200 is pulled out from the ventral side and the hook tape 32 is detached from the liquid pervious top sheet 2. This allows the hook tape 32 to be easily peeled off. The angle $\theta_1$ of the hook shaped projections F with respect to the base material sheet 32s is preferably 30 to 70 degrees.

The absorbent pad 200 of the present invention, in the product state, may have the attachment panel 31 folded back at the folding portion 31c and the extended portion 31a attached at the underside surface to the temporary tack portion 33, or, in the product state, may have the attachment panel 31 open so that, for use, the user folds back the attachment panel 31 at the folding portion 31c, attaches the extended portion 31a at the underside surface to the temporary tack portion 33, and then attaches the absorbent pad 200 to the diaper or the lower-body underwear. If the absorbent pad 200 has in the product state the attachment panel 31 folded back at the folding portion 31c and the extended portion 31a attached at the underside surface to the temporary tack portion 33, the temporary tack portion 33 needs no protection sheet, which can decrease a component count and therefore reduce manufacturing costs.

INDUSTRIAL APPLICABILITY

The present invention can be used in combination with disposable diapers and also be applied to sanitary napkins as far as the present invention constitutes an absorbent pad.

Figure 1:
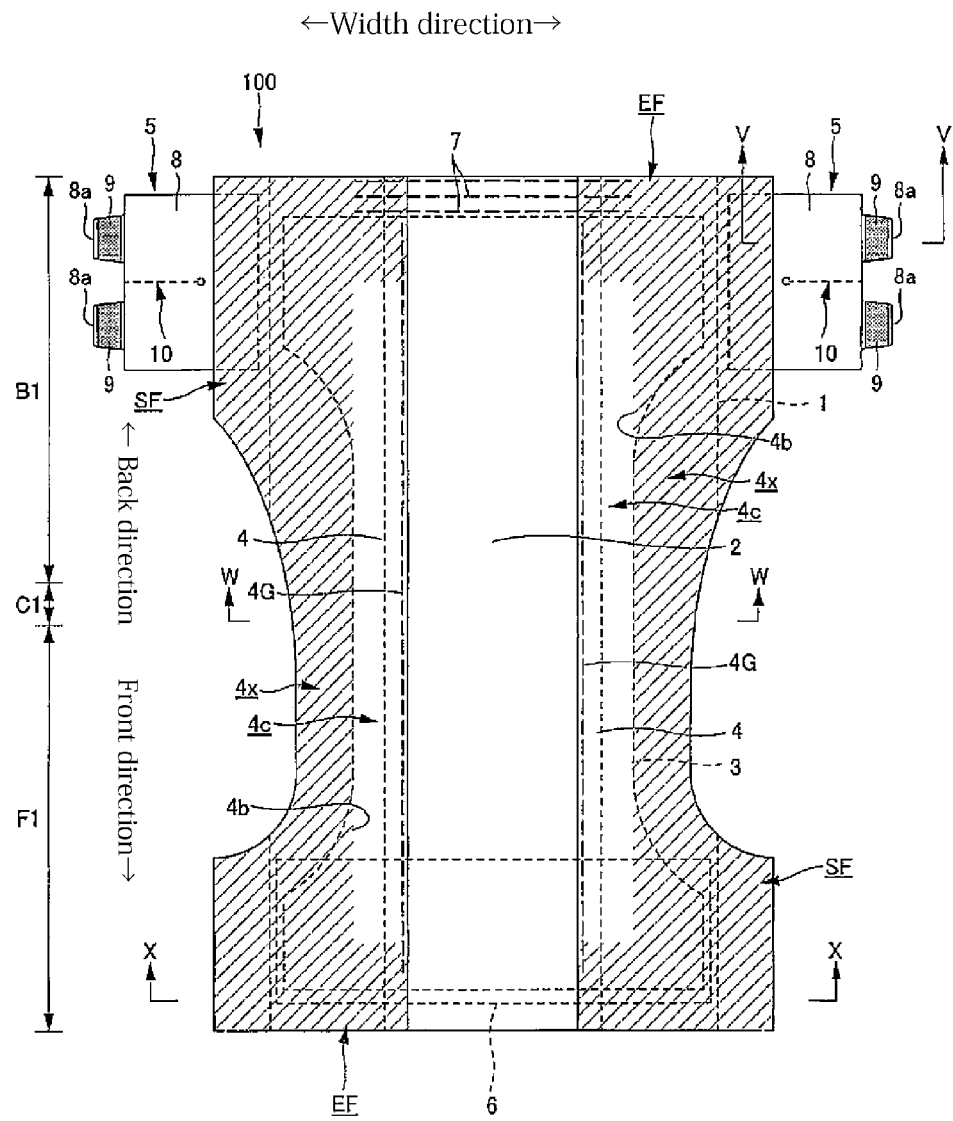
FIG. 1 is a plane view showing an inner surface of a tape-type disposable diaper in an open state.
Figure 2:
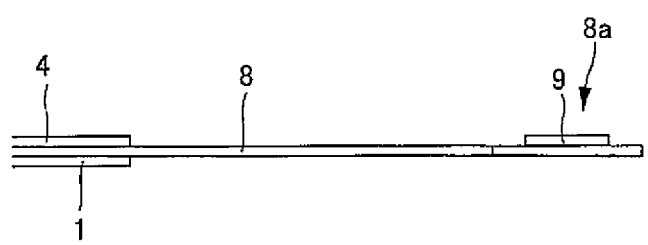
FIG. 2 is a cross-section view of FIG. 1 taken along line V-V.
Figure 3:
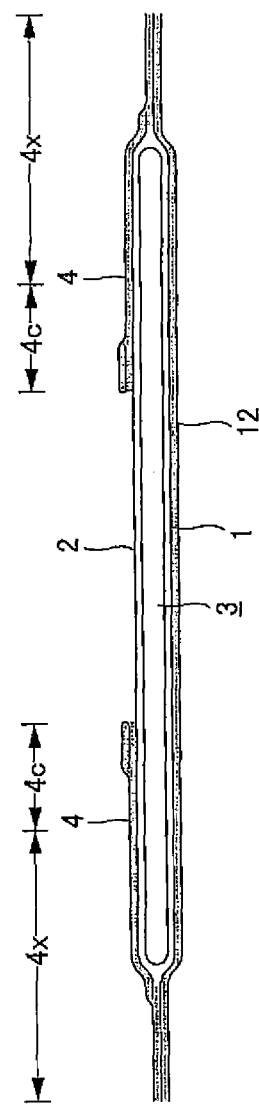
FIG. 3 is a cross-section view of FIG. 1 taken along line X-X.
Figure 4:
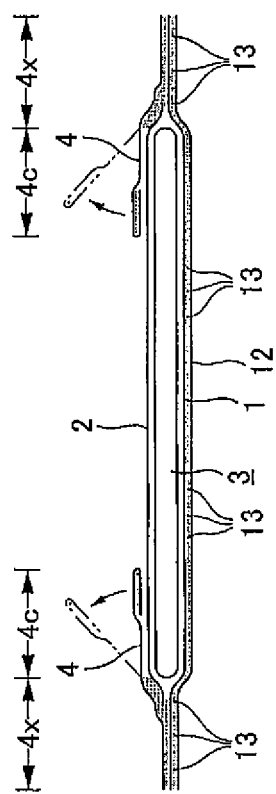
FIG. 4 is a cross-section view of FIG. 1 taken along line W-W.
Figure 5:
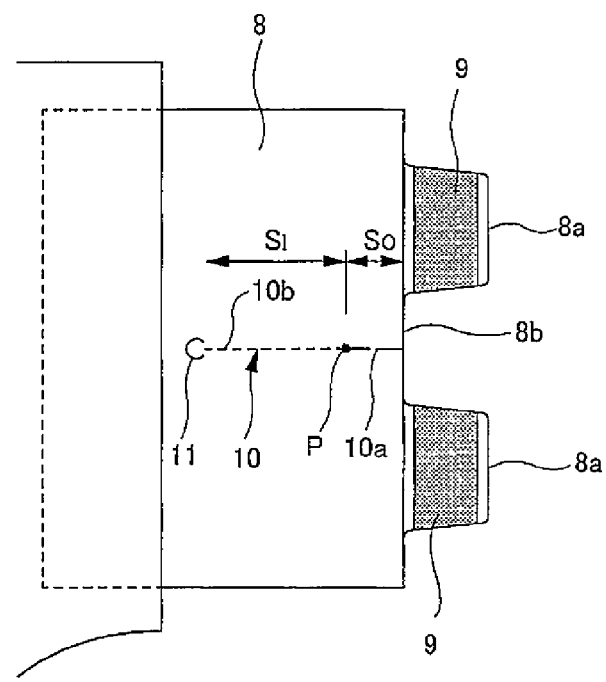
FIG. 5 is an enlarged plane view of major components.
Figure 6:
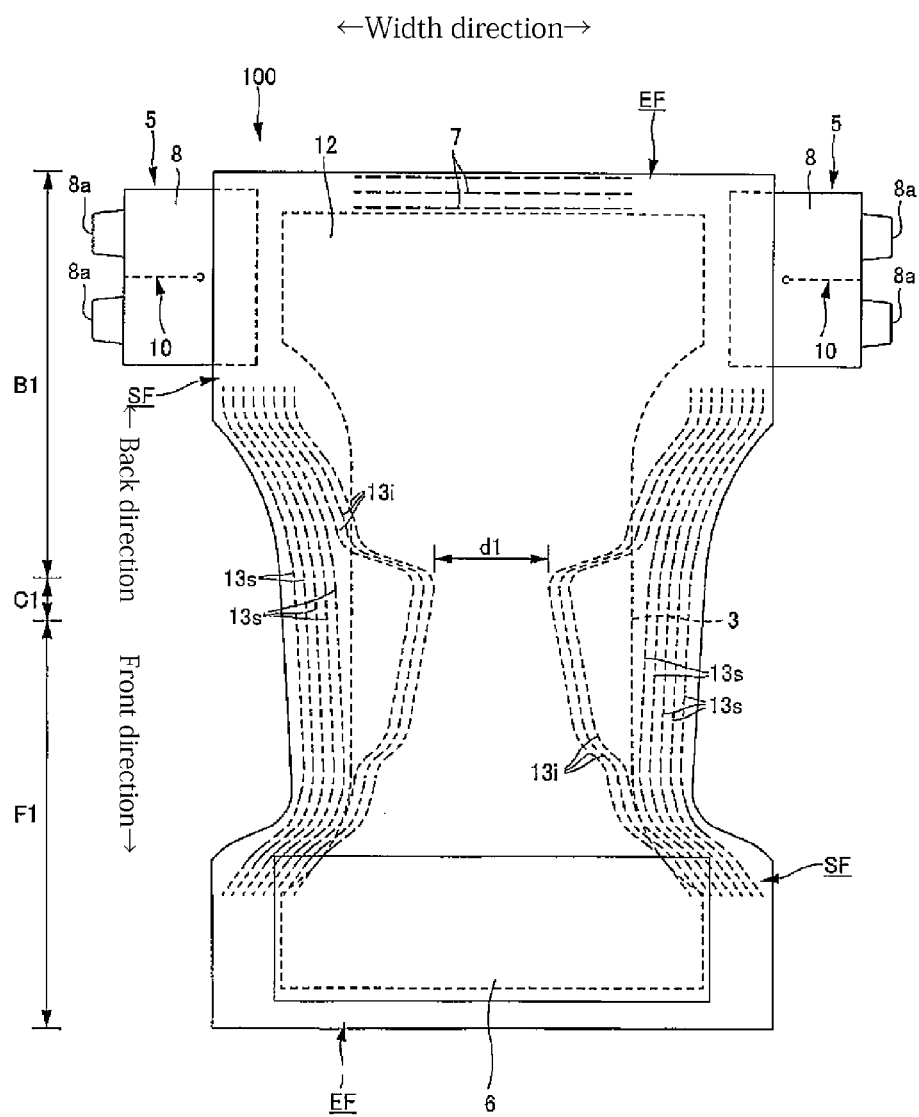
FIG. 6 is a plane view showing an outer surface of the tape-type disposable diaper in the open state.
Figure 7:
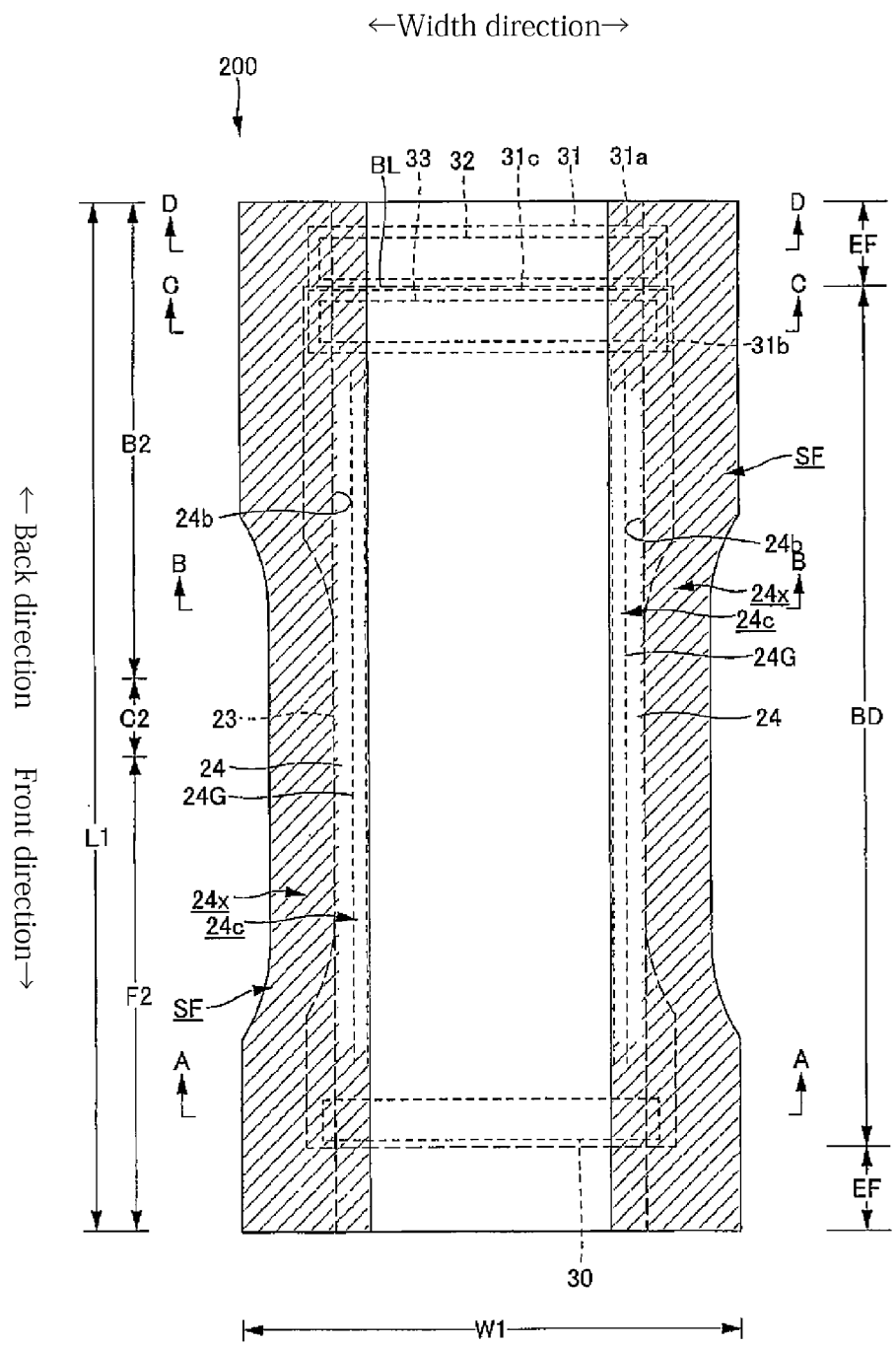
FIG. 7 is a plane view showing a top surface of an absorbent pad in an open state.
Figure 8:
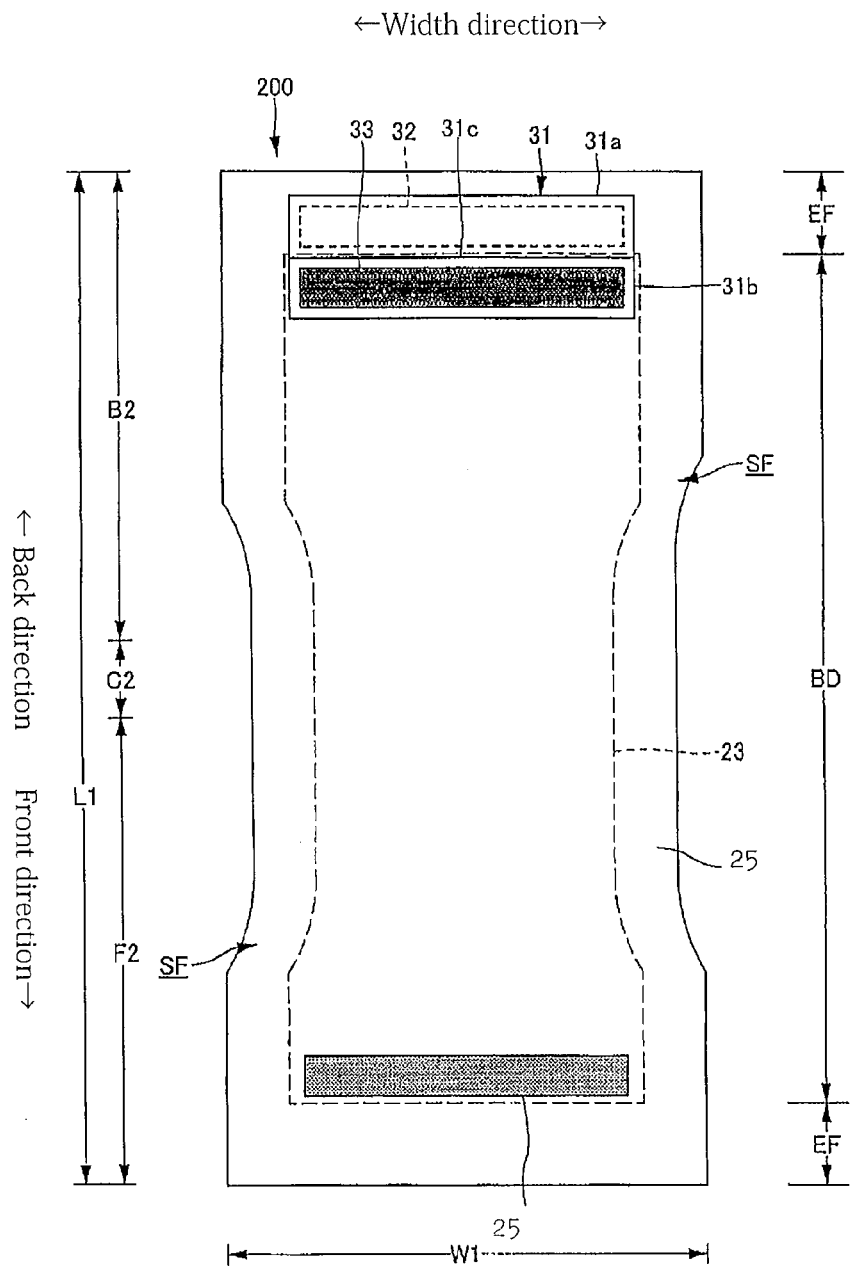
FIG. 8 is a plane view showing an underside surface of the absorbent pad in the open state.
Figure 9:
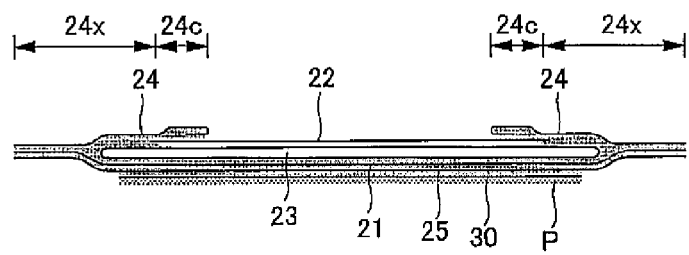
FIG. 9 is a cross-section view of FIG. 7 taken along line A-A.
Figure 10:
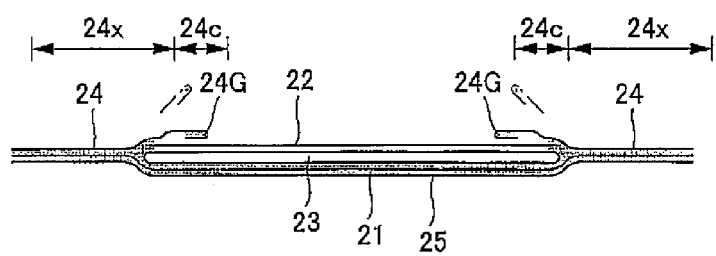
FIG. 10 is a cross-section view of FIG. 7 taken along line B-B.
Figure 11:
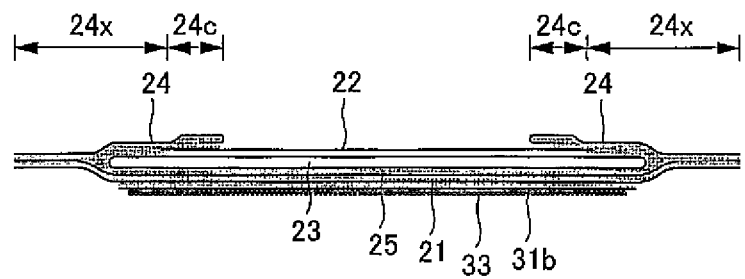
FIG. 11 is a cross-section view of FIG. 7 taken along line C-C.
Figure 12:
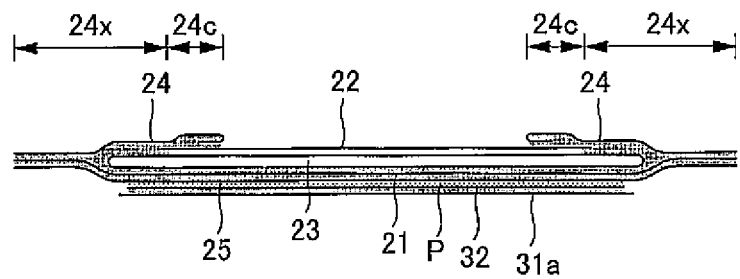
FIG. 12 is a cross-section view of FIG. 7 taken along line D-D.
Figure 13:
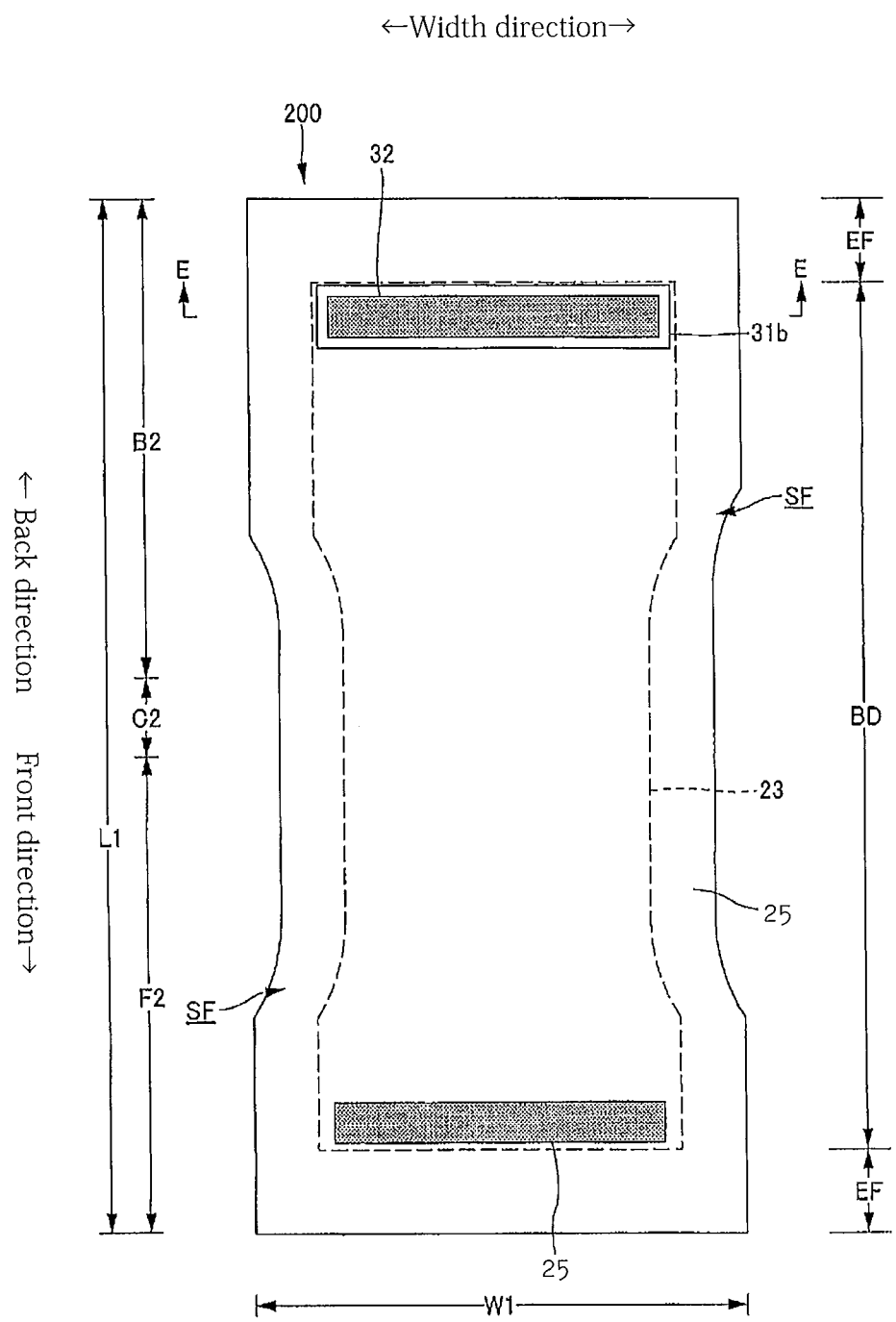
FIG. 13 is a plane view showing the underside surface of the absorbent pad in the open state with the attachment panel folded back.
Figure 14:
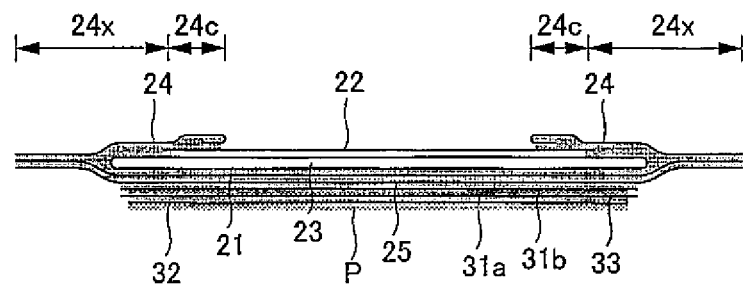
FIG. 14 is a cross-section view of FIG. 7 taken along line E-E.
Figure 15:
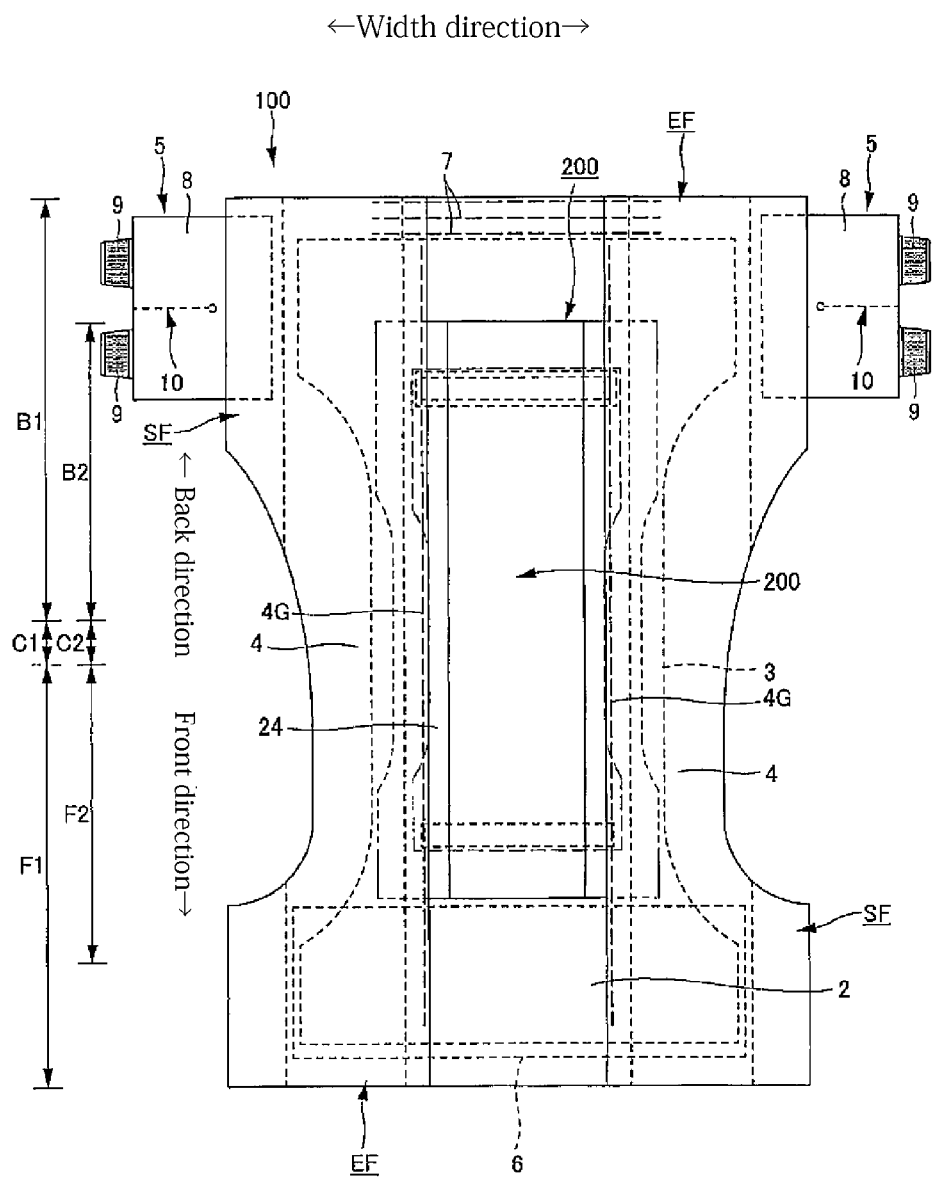
FIG. 15 is a plane view showing the top surface of the tape-type disposable diaper in the open state with the absorbent pad attached.
Figure 16:
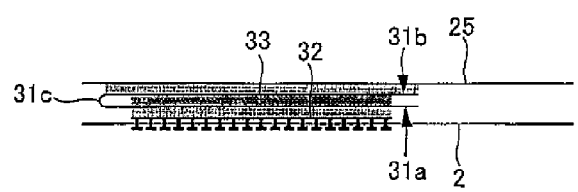
FIG. 16 is a diagram showing movements of a hook tape when being detached from a liquid pervious top sheet.
Figure 16:
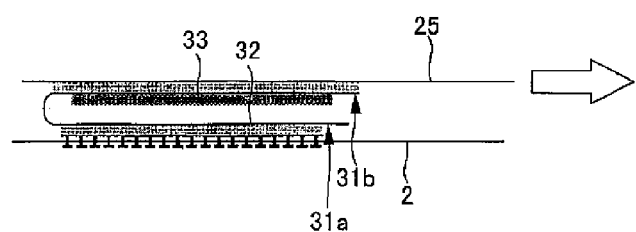
Figure 16:
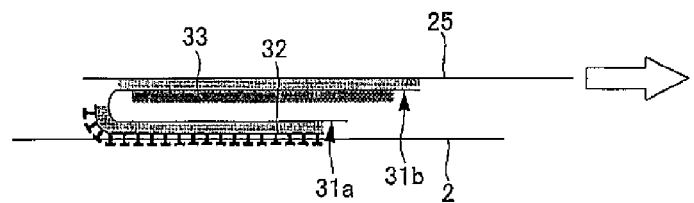
Figure 17:
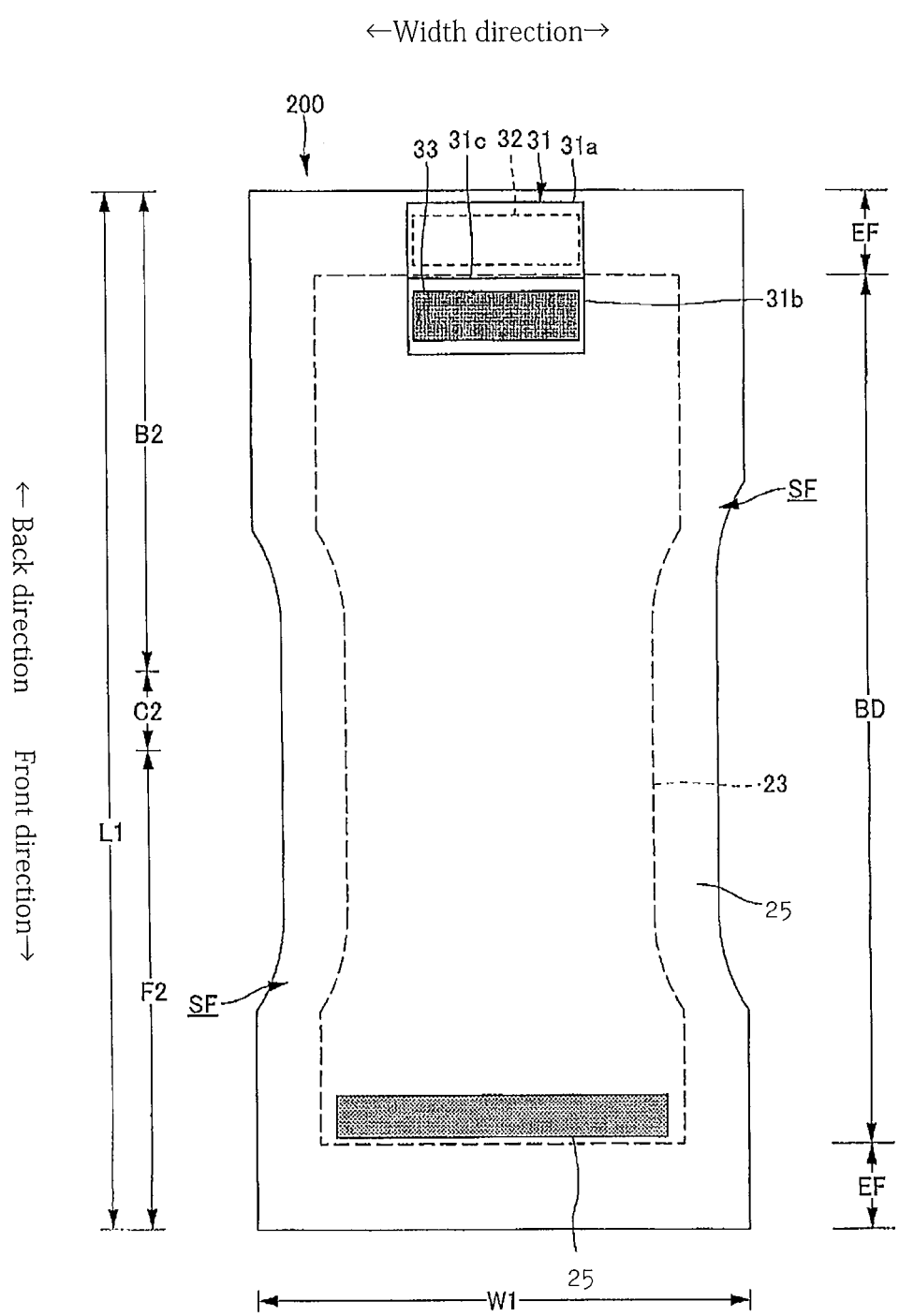
FIG. 17 is a plane view showing the underside surface of the absorbent pad in the open state.
Figure 18:
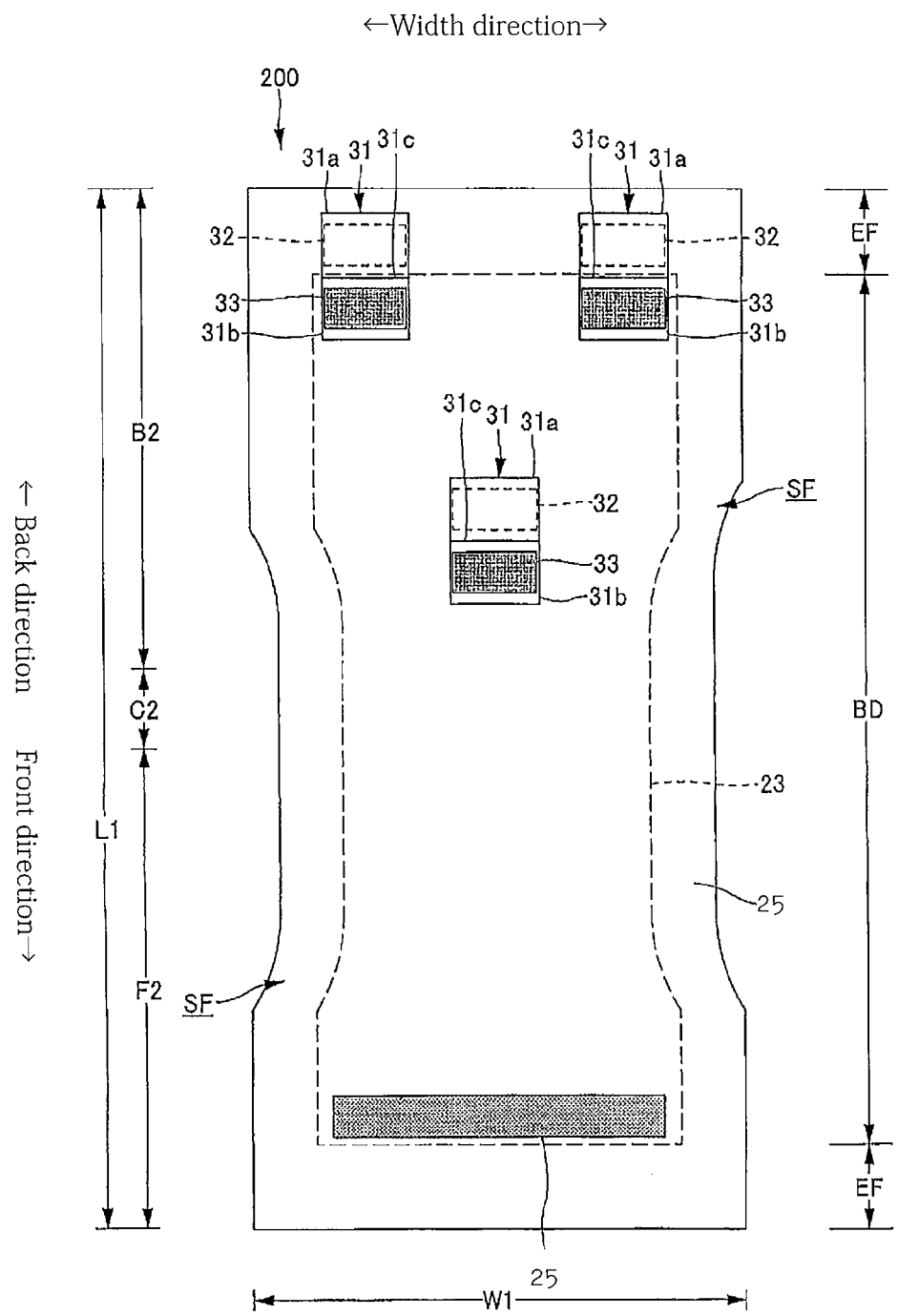
FIG. 18 is a plane view showing the underside surface of the absorbent pad in the open state.
Figure 19:
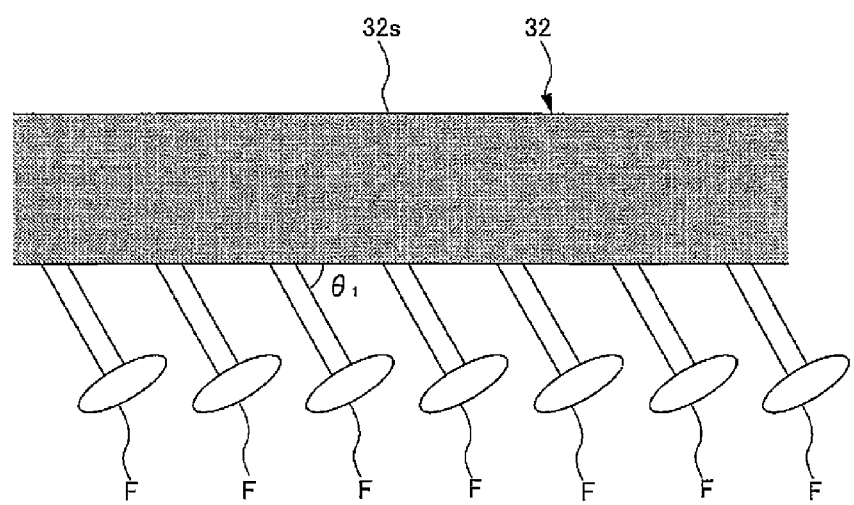
FIG. 19 is an enlarged view of the hook tape with the attachment panel folded back.

BRIEF DESCRIPTION OF NUMERALS 1, 21 . . . Liquid impervious back sheet, 2, 22 . . . Liquid pervious top sheet, 3, 23 . . . Absorbent body, 4, 24 . . . Barrier sheet, 5 . . . Fastening tape, 6 . . . Target tape, 7 . . . Resilient and elastic member, 8 . . . Base material sheet, 9 . . . Hook tape, 10 . . . Perforation, 12 . . . Outer sheet, 13i, 13s . . . Resilient and elastic member, 25 . . . Outer sheet, 30 . . . Hook tape, 31 . . . Attachment panel, 32 . . . Hook tape, 33 . . . Temporary tack portion, 100 . . . Tape-type disposable diaper, 200 . . . Absorbent pad.

The invention claimed is:
1. An absorbent pad for use in combination with a diaper, the absorbent pad comprising: a liquid permeable topsheet, an absorbent body, and a liquid impermeable backsheet having a garment facing surface and user facing surface, the absorbent pad having a ventral side portion extending from a crotch portion to a ventral side and a back side portion extending from the crotch portion to a back side, the absorbent pad further including:

an attachment panel including: a base portion fixed to an underside surface of the absorbent pad; an extended portion that extends from a rear edge of the base portion; and a hook tape that is fixed to the extended portion, said attachment panel having a first surface and second surface opposite the first surface, wherein the first surface is, on said base portion, fixed to the garment facing surface of the liquid impermeable backsheet and also, on said extended portion, fixed to said hook tape, wherein the hook tape has a large number of hook shaped projections opposite a side of the hook tape where the hook tape is fixed to the extended portion where said attachment panel is adapted to be attached to the diaper through said hook tape when said attachment panel is in a folded position, said folded position being the position where the second surface of the attachment panel in the extended portion contacts the second surface of the attachment panel in the base portion, and wherein the rear edge of the base portion is generally parallel with the width of the pad such that the extended portion extends in a direction generally perpendicular to the width of the pad.

2. The absorbent pad according to claim 1, wherein, in the folded state, the extended portion is temporarily tacked to an opposite surface thereof in a detachable manner.

3. The absorbent pad according to claim 1, wherein the attachment panel is provided at the back side portion.

4. The absorbent pad according to claim 1 wherein, when the extended portion of the attachment panel is unfolded backward, the entire surface of the hook tape having the hook shaped projections is opposed to the underside surface of the absorbent pad, so as not to be exposed to the body of a wearer.

5. The absorbent pad according to claim 1, wherein the hook shaped projections incline toward a leading edge of the extended portion.

6. The absorbent pad according to claim 2, wherein the attachment panel is provided at the back side portion.

7. The absorbent pad according to claim 2, wherein, when the extended portion of the attachment panel is unfolded backward, the entire surface of the hook tape having the hook shaped projections is opposed to the underside surface of the absorbent pad, so as not to be exposed to the body of a wearer.

8. The absorbent pad according to claim 3, wherein, when the extended portion of the attachment panel is unfolded backward, the entire surface of the hook tape having the hook shaped projections is opposed to the underside surface of the absorbent pad, so as not to be exposed to the body of a wearer.

9. The absorbent pad according to claim 1, wherein, in the folded state, the extended portion is temporarily tacked to an opposite surface thereof in a detachable manner, wherein the attachment panel is provided at the back side portion, and wherein, when the extended portion of the attachment panel is unfolded backward, the entire surface of the hook tape having the hook shaped projections is opposed to the underside surface of the absorbent pad, so as not to be exposed to the body of a wearer.

10. The absorbent pad according to claim 2, wherein the hook shaped projections incline toward a leading edge of the extended portion.

11. The absorbent pad according to claim 3, wherein the hook shaped projections incline toward a leading edge of the extended portion.

12. The absorbent pad according to claim 4, wherein the hook shaped projections incline toward a leading edge of the extended portion.

13. The absorbent pad according to claim 2, wherein the attachment panel is provided at the back side portion, wherein, when the extended portion of the attachment panel is unfolded backward, the entire surface of the hook tape having the hook shaped projections is opposed to the underside surface of the absorbent pad, so as not to be exposed to the body of a wearer, and wherein the hook shaped projections incline toward a leading edge of the extended portion.

14. The absorbent pad according to claim 2, wherein, when the extended portion of the attachment panel is unfolded backward, the entire surface of the hook tape having the hook shaped projections is opposed to the underside surface of the absorbent pad, so as not to be exposed to the body of a wearer, and wherein the hook shaped projections incline toward a leading edge of the extended portion.

15. The absorbent pad according to claim 2, wherein the attachment panel is provided at the back side portion and wherein the hook shaped projections incline toward a leading edge of the extended portion.

16. The absorbent pad according to claim 2, wherein the attachment panel is provided at the back side portion and wherein, when the extended portion of the attachment panel is unfolded backward, the entire surface of the hook tape having the hook shaped projections is opposed to the underside surface of the absorbent pad, so as not to be exposed to the body of a wearer.

17. In combination, an absorbent pad and a diaper, where the absorbent pad includes a liquid permeable topsheet, an absorbent body, and a liquid impermeable backsheet having a garment facing surface and user facing surface, the absorbent pad having a ventral side portion extending from a crotch portion to a ventral side and a back side portion extending from the crotch portion to a back side, the absorbent pad further including:

an attachment panel including: a base portion fixed to an underside surface of the absorbent pad; an extended portion that extends from a rear edge of the base portion; and a hook tape that is fixed to the extended portion, said attachment panel having a first surface and second surface opposite the first surface, wherein the first surface is, on said base portion, fixed to the garment facing surface of the liquid impermeable backsheet and also, on said extended portion, fixed to said hook tape, wherein the hook tape has a large number of hook shaped projections opposite a side of the hook tape where the hook tape is fixed to the extended portion, where said attachment panel is folded so that the second surface of attachment panel in the extended portion contacts the second surface of the attachment panel in the base portion, and where said hook tape is attached to the diaper, and wherein the rear edge of the base portion is generally parallel with the width of the pad such that the extended portion extends in a direction generally perpendicular to the width of the pad.

* * * * *